(12) United States Patent
Noda

(10) Patent No.: US 12,036,061 B2
(45) Date of Patent: Jul. 16, 2024

(54) IMAGE PROCESSING APPARATUS AND CONTROL METHOD THEREOF, RADIOGRAPHY APPARATUS, AND COMPUTER-READABLE STORAGE MEDIUM

(71) Applicant: CANON KABUSHIKI KAISHA, Tokyo (JP)

(72) Inventor: Takeshi Noda, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 366 days.

(21) Appl. No.: 17/648,477

(22) Filed: Jan. 20, 2022

(65) Prior Publication Data
US 2022/0142597 A1 May 12, 2022

Related U.S. Application Data

(63) Continuation of application No. PCT/JP2020/027397, filed on Jul. 14, 2020.

(30) Foreign Application Priority Data

Aug. 2, 2019 (JP) ................................. 2019-143310

(51) Int. Cl.
*A61B 6/00* (2024.01)
*G01N 23/04* (2018.01)
*G06T 7/00* (2017.01)
*A61B 6/50* (2024.01)

(52) U.S. Cl.
CPC ............ *A61B 6/5217* (2013.01); *G01N 23/04* (2013.01); *G06T 7/97* (2017.01); *A61B 6/481* (2013.01); *A61B 6/505* (2013.01); *G01N 2223/401* (2013.01); *G01N 2223/423* (2013.01);
(Continued)

(58) Field of Classification Search
CPC ....... A61B 6/5217; A61B 6/481; A61B 6/505; A61B 6/482; G01N 23/04; G01N 2223/401; G01N 2223/423; G06T 7/97; G06T 2207/10116; G06T 2207/20104; G06T 5/92; G06T 2207/10016; G06T 2207/20182; G06T 2207/20224; G06T 2207/30004; G06T 5/50
See application file for complete search history.

(56) References Cited

U.S. PATENT DOCUMENTS

| | | |
|---|---|---|
| 8,355,594 B2 | 1/2013 | Noda |
| 8,655,034 B2 | 2/2014 | Noda |
| 8,744,210 B2 | 6/2014 | Noda |

(Continued)

FOREIGN PATENT DOCUMENTS

| | | |
|---|---|---|
| JP | 8-266529 A | 10/1996 |
| JP | 2010-512826 A | 4/2010 |

(Continued)

*Primary Examiner* — Courtney D Thomas
(74) *Attorney, Agent, or Firm* — VENABLE LLP

(57) ABSTRACT

An image processing apparatus generates a material characteristic image based on a plurality of radiation images corresponding to a plurality of radiation energies, and estimates at least one of the plurality of radiation energies at a second timing using a plurality of material characteristic images including a material characteristic image generated based on a plurality of radiation images acquired at a first timing and a material characteristic image generated based on a plurality of radiation images acquired at the second timing later than the first timing.

20 Claims, 5 Drawing Sheets

(52) U.S. Cl.
CPC ............... *G06T 2207/10116* (2013.01); *G06T 2207/20104* (2013.01)

(56) References Cited

U.S. PATENT DOCUMENTS

| | | |
|---|---|---|
| 8,923,589 B2 | 12/2014 | Noda |
| 9,014,450 B2 | 4/2015 | Noda |
| 9,820,713 B2 | 11/2017 | Noda |
| 9,953,414 B2 | 4/2018 | Noda |
| 2019/0320993 A1 | 10/2019 | Noda et al. |
| 2020/0163630 A1 | 5/2020 | Noda et al. |
| 2021/0055233 A1 | 2/2021 | Noda et al. |
| 2021/0118193 A1 | 4/2021 | Torii et al. |
| 2021/0236078 A1 | 8/2021 | Noda |
| 2022/0047238 A1 | 2/2022 | Terui et al. |

FOREIGN PATENT DOCUMENTS

| | | |
|---|---|---|
| JP | 2011-104103 A | 6/2011 |
| JP | 2017-86901 A | 5/2017 |
| JP | 2018-57669 A | 4/2018 |
| WO | 2008/072175 A1 | 6/2008 |

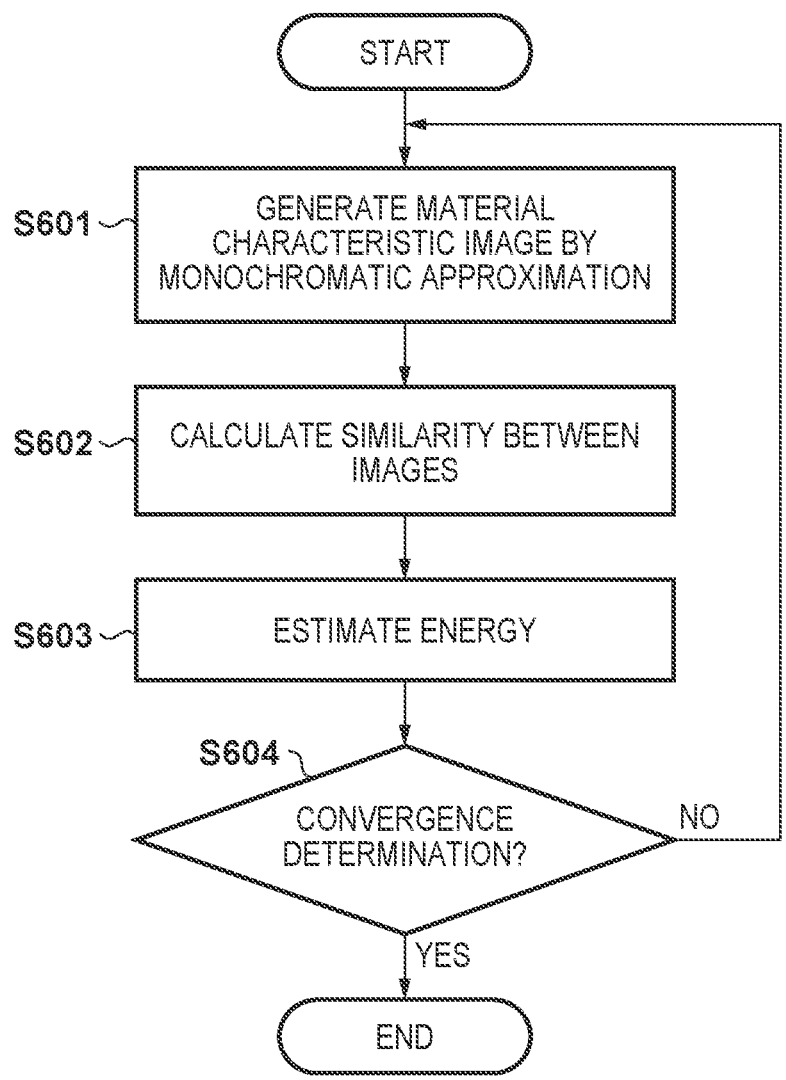

IMAGE PROCESSING APPARATUS AND CONTROL METHOD THEREOF, RADIOGRAPHY APPARATUS, AND COMPUTER-READABLE STORAGE MEDIUM

CROSS-REFERENCE TO RELATED APPLICATIONS

This application is a Continuation of International Patent Application No. PCT/JP2020/027397, filed Jul. 14, 2020, which claims the benefit of Japanese Patent Application No. 2019-143310, filed Aug. 2, 2019, both of which are hereby incorporated by reference herein in their entirety.

BACKGROUND OF THE INVENTION

Field of the Invention

The present invention relates to an image processing apparatus and control method thereof, a radiography apparatus, and a computer-readable storage medium.

Background Art

Radiography apparatuses that use a flat panel detector (hereinafter abbreviated as "FPD") have become prevalent as imaging apparatuses used in medical imaging diagnosis that uses radiation. Since images captured using an FPD can be a target of digital image processing, various applications for processing the captured images have been developed and put into practical use.

PTL. 1 discloses a method for determining the tube voltage to be irradiated based on the thickness of the body of a subject in a configuration for obtaining an energy subtraction image by irradiating radiation of two tube voltages. In addition, PTL. 2 discloses a method for correcting, using a reference, a shift over time in the calibration curve for determining a bone mineral amount in a bone mineral amount analysis that uses energy subtraction.

CITATION LIST

PTL. 1 Japanese Patent Laid-Open No. 2011-104103
PTL. 2 Japanese Patent Laid-Open No. 08-266529

If the energy of radiation irradiated fluctuates in energy subtraction, which uses radiation of a plurality of energies, an energy subtraction image may become unstable, hindering diagnosis and treatment. For example, in vascular imaging apparatuses, an application of energy subtraction for obtaining, during treatment, an image (moving image) in which a contrast-enhanced blood vessel is separated may be considered. In such fluoroscopic imaging, an auto brightness control (ABC) function for maintaining a constant amount of radiation passing through the subject on the apparatus side is provided in order to ensure the stability of image quality in imaging. Since ABC automatically changes the tube voltage, tube current, and pulse width of the radiation generator, the energy of the radiation irradiated by the radiation generator fluctuates when ABC functions. As described above, since fluctuations in radiation energy cause energy subtraction images to be unstable, fluoroscopic images that use energy subtraction images become unstable.

Although there is a possibility that fluoroscopic images may be stabilized against fluctuations in radiation energy by applying a method described in PTL. 2, there is a practical problem. That is, in the method described in PTL. 2, it is necessary to place a reference in the irradiation field; however, a case may occur in which the reference overlaps with the subject during shooting. When the reference overlaps with the subject, the calibration curve cannot be corrected and stable energy subtraction cannot be performed.

SUMMARY OF THE INVENTION

The present invention provides a technique for performing stable energy subtraction by improving the accuracy of the energy (spectrum) of radiation used in energy subtraction.

According to one aspect of the present invention, there is provided an image processing apparatus comprising: a generation unit configured to generate a material characteristic image based on a plurality of radiation images corresponding to a plurality of radiation energies; and an estimation unit configured to estimate at least one of the plurality of radiation energies at a second timing using a plurality of material characteristic images including a material characteristic image that the generation unit generated based on a plurality of radiation images acquired at a first timing and a material characteristic image that the generation unit generated based on a plurality of radiation images acquired at the second timing later than the first timing.

According to another aspect of the present invention, there is provided a radiography apparatus comprising: a radiation detection unit configured to capture a plurality of radiation images corresponding to a plurality of radiation energies; a generation unit configured to generate a material characteristic image based on the plurality of radiation images captured by the radiation detection unit; and an estimation unit configured to estimate at least one of the plurality of radiation energies at a second timing using a plurality of material characteristic images including a material characteristic image that the generation unit generated based on the plurality of radiation images that the radiation detection unit acquired at a first timing and a material characteristic image that the generation unit generated based on the plurality of radiation images that the radiation detection unit acquired at the second timing later than the first timing.

According to another aspect of the present invention, there is provided a method of controlling an image processing apparatus, the method comprising: generating a material characteristic image based on a plurality of radiation images corresponding to a plurality of radiation energies; and estimating at least one of the plurality of radiation energies at a second timing using a plurality of material characteristic images including a material characteristic image generated in the generating based on a plurality of radiation images acquired at a first timing and a material characteristic image generated in the generating based on a plurality of radiation images acquired at the second timing later than the first timing.

Further features of the present invention will become apparent from the following description of exemplary embodiments with reference to the attached drawings.

BRIEF DESCRIPTION OF THE DRAWINGS

FIG. 6 is a flowchart illustrating processing by an image processing unit of a second embodiment.

DESCRIPTION OF THE EMBODIMENTS

Figure 1:
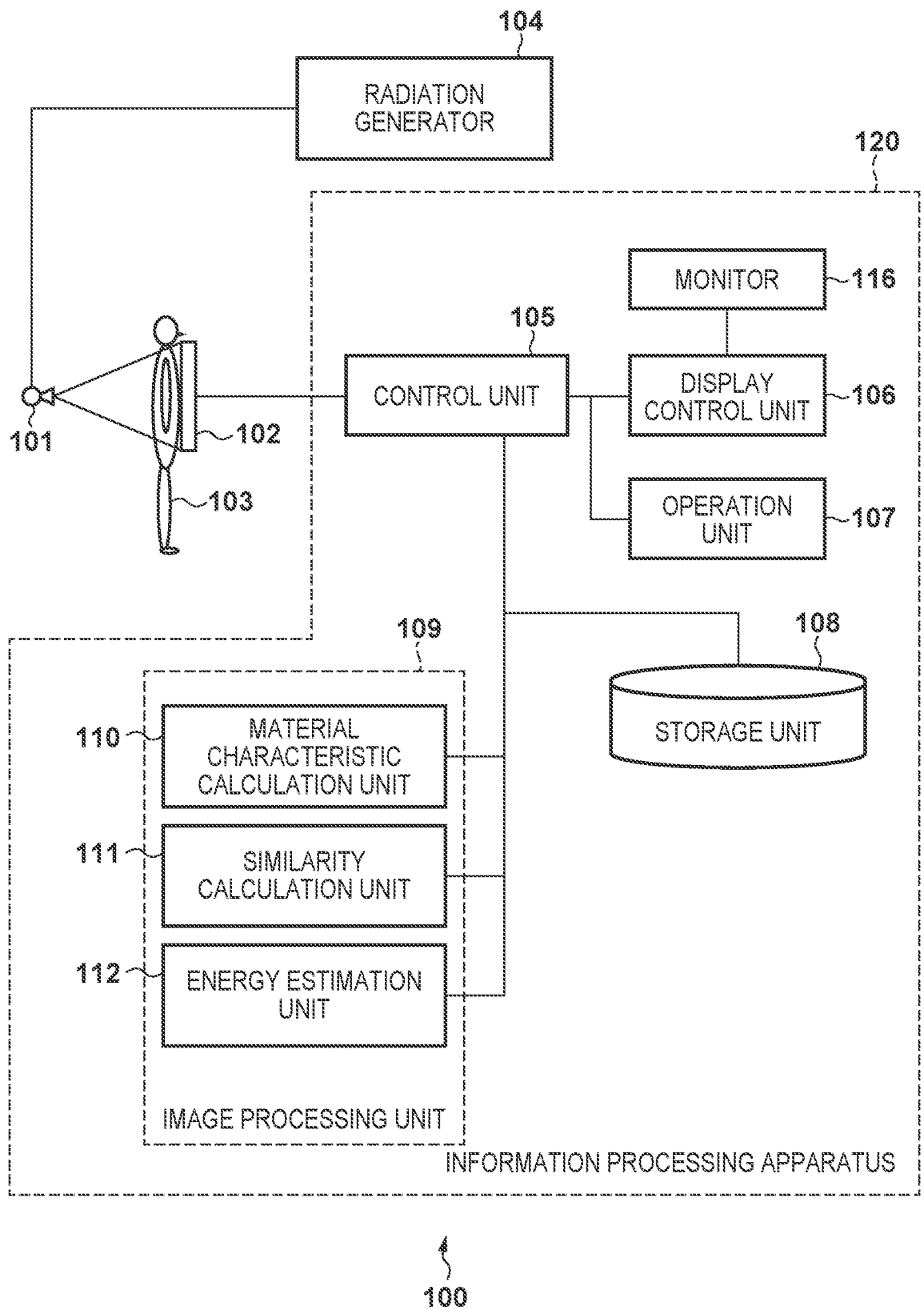
FIG. 1 is a diagram illustrating an example of a configuration of a radiation imaging system according to a first embodiment.

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted.

First Embodiment

FIG. 1 is a block diagram illustrating an example of a configuration of a radiation imaging system 100 according to the first embodiment. The radiation imaging system 100 includes a radiation generator 104, a radiation tube 101, a flat panel detector (hereinafter, FPD 102), and an information processing apparatus 120. The configuration of the radiation imaging system 100 is also simply referred to as a radiography apparatus.

The radiation generator 104 generates radiation by applying a high voltage pulse to the radiation tube 101 via user operation on an exposure switch (not illustrated). Note that in this specification, the term radiation may include, in addition to X-rays, α-rays, β-rays, γ-ray particle rays, cosmic rays, and the like, for example. The type of radiation is not particularly limited in the embodiment, but medical imaging diagnosis mainly uses X-rays. The radiation generated from the radiation tube 101 irradiates a subject 103, and some of it passes through the subject 103 and reaches the FPD 102.

The FPD 102 acquires a radiation image by accumulating charges based on image signals and transfers the acquired radiation image to the information processing apparatus 120. The FPD 102 has a radiation detection unit (not illustrated) which comprises a pixel array for generating signals corresponding to radiation and a drive unit (not illustrated) for reading image signals by driving the radiation detection unit. The radiation detection unit detects, as image signals, radiation that has passed through the subject 103 and reached the detection surface of the radiation detection unit. In the radiation detection unit, pixels for outputting a signal corresponding to incident light are arranged in an array (two-dimensional region). The photoelectric conversion element of each pixel converts radiation converted into visible light by a scintillator (phosphor) into an electric signal and outputs it as an image signal. As described above, the radiation detection unit is configured to detect radiation that has passed through the subject 103 and acquire image signals (radiation image). The drive unit of the FPD 102 outputs, to the information processing apparatus 120 (control unit 105), the image signals (radiation image) that have been read from the radiation detection unit in accordance with an instruction from the control unit 105.

The information processing apparatus 120 processes the radiation image in which the FPD 102 has captured the subject. The information processing apparatus 120 includes the control unit 105, a display control unit 106, an operation unit 107, a storage unit 108, an image processing unit 109, and a monitor 116.

The control unit 105 includes one or a plurality of processors (not illustrated) and realizes various controls of the information processing apparatus 120 by executing programs stored in the storage unit 108. The storage unit 108 stores various programs to be executed by the control unit 105 and the like. The storage unit 108 is configured by, for example, a ROM (Read Only Memory), a RAM (Random Access Memory), a hard disk, or the like. In addition to the above programs, the storage unit 108 can store, for example, images outputted from the control unit 105, images processed by the image processing unit 109, and results of calculation in the image processing unit 109.

The image processing unit 109 processes the radiation image acquired from the FPD 102. The image processing unit 109 has a material characteristic calculation unit 110, a similarity calculation unit 111, and an energy estimation unit 112 as functional components. These functional components may be realized by the processor of the control unit 105 executing predetermined programs or may be realized by one or a plurality of processors included in the image processing unit 109 executing programs read from the storage unit 108. The processors of the control unit 105 and the image processing unit 109 are configured by, for example, CPUs (central processing units). In addition, some or all of the functional units of the control unit 105 and the image processing unit 109 may be implemented by an integrated circuit or the like that performs the same functions. The information processing apparatus 120 may include as an internal configuration a graphic control unit such as a GPU (Graphics Processing Unit), a communication unit such as a network card, and an input/output control unit such as a keyboard, a display, and a touch panel, and the like.

The display control unit 106 displays on the monitor 116 radiation images (digital images) that the control unit 105 received from the FPD 102, images processed by the image processing unit 109, and the like. The operation unit 107 provides a user interface (not illustrated) for the user to input instructions for the image processing unit 109 and the FPD 102. The control unit 105 receives user instruction inputs for the image processing unit 109 and the FPD 102 via the user interface.

In the above configuration, the radiation generator 104 applies a high voltage to the radiation tube 101 and causes the radiation tube 101 to continuously or intermittently irradiate radiation on the subject 103. The FPD 102 generates a plurality of radiation images by the radiation tube 101 irradiating radiation. In the present embodiment, the radiation generator 104 emits two types of radiation, high energy and low energy, from the radiation tube 101, and the FPD 102 generates a high-energy radiation image $XH_n$ and a low-energy radiation image $XL_n$. Here, n denotes a moving image frame number. However, three or more types of radiation images may be generated in one frame by performing radiation irradiation of three or more types of radiation energy. The control unit 105 acquires a high-energy radiation image $XH_n$ and a low-energy radiation image $XL_n$ from the FPD 102 and displays these on the monitor 116 via the display control unit 106. The radiation images displayed on the monitor 116 can be used for diagnosis or therapy. The control unit 105 stores the radiation images in the storage unit 108 and transmits the stored radiation images to the image processing unit 109.

The energy of radiation generated by the radiation tube 101 can be set and changed by the tube voltage/pulse width that the radiation generator 104 sets in the radiation tube 101. For example, a high voltage pulse of 120 kV is applied to the radiation tube 101 when irradiating with high-energy radiation and a high voltage pulse of 80 kV is applied to the radiation tube 101 when irradiating with low-energy radiation. In energy subtraction, a larger difference in these energies is more preferable, but appropriate energies are selected in consideration of the thickness of the body and the radiation exposure amount of the subject.

As the FPD 102, a device capable of acquiring, in a single radiation irradiation, radiation images corresponding to a plurality of energies may be used. In this type of the FPD 102, sampling is performed a plurality of times for a single radiation irradiation from the radiation tube 101. That is, the FPD 102 can obtain a high-energy radiation image $XH_n$ and a low-energy radiation image $XL_n$ in a single radiation irradiation by performing instantaneous sampling when the high voltage pulse applied to the radiation tube 101 is rising and when it is falling. Such an imaging method is effective in preventing motion artifacts from being generated in a subject that move considerably, such as the heart.

Further, a configuration may also be taken so as to acquire a radiation image of a plurality of energies from a single radiation irradiation from the radiation tube 101 using an FPD 102 in which detectors of two layers are in a layered structure. In this case, beam hardening occurs due to radiation passing through the detector of the first layer, increasing the energy in the detector of the second layer. Therefore, in a single radiation irradiation, it is possible to obtain the low-energy radiation image $XL_n$ with the output of a detector of a first layer and the high-energy radiation image $XH_n$ with the output of a detector of a second layer. Such an imaging system is effective in that radiation images of a plurality of energies are obtained in a single radiation irradiation without particularly controlling the radiation tube 101. The occurrence of motion artifacts is also suppressed.

The material characteristic calculation unit 110 obtains an image of the thickness of a material by solving a nonlinear simultaneous equation obtained based on radiation attenuation corresponding to at least two types of energies and at least two radiation images corresponding to at least two types of energies. More specifically, the material characteristic calculation unit 110 of the present embodiment generates a material characteristic image by solving a weighted difference or inverse problem using a high-energy radiation image $XH_n$ and a low-energy radiation image $XL_n$. Here, the material characteristic image refers to, for example, an image in which the thickness of fat, bone, a contrast agent, or the like constituting the subject is used as a pixel value or an image in which the effective atomic number of the material constituting the subject is used as a pixel value.

The similarity calculation unit 111 calculates the similarity between the material characteristic image generated by the material characteristic calculation unit 110 at a first timing and the material characteristic image generated by the material characteristic calculation unit 110 at a second timing different from the first timing. Here, the second timing is a timing later in time than the first timing. In the present embodiment, the sum of squared differences (SSD) of pixel values is used as a similarity index, but the present invention is not limited thereto. For example, common indices for comparing the similarities of images such as the sum of absolute differences (SAD) of pixel values, normalized cross-correlation (NCC), and the like can be used.

The energy estimation unit 112 estimates the radiation energy (spectrum) to be used by the material characteristic calculation unit 110 such that the similarity indicated by the index calculated by the similarity calculation unit 111 is as high as possible, that is, the sum of squared differences which is an index decreases. The energy estimation unit 112 performs an optimization operation in order to obtain such radiation energy. By this optimization operation, the energy estimation unit 112 estimates the energy spectrum of the voltage that the radiation generator 104 applied to the radiation tube 101 or the radiation irradiated from the radiation tube 101. Details of the optimization calculation will be described later.

Figure 2:
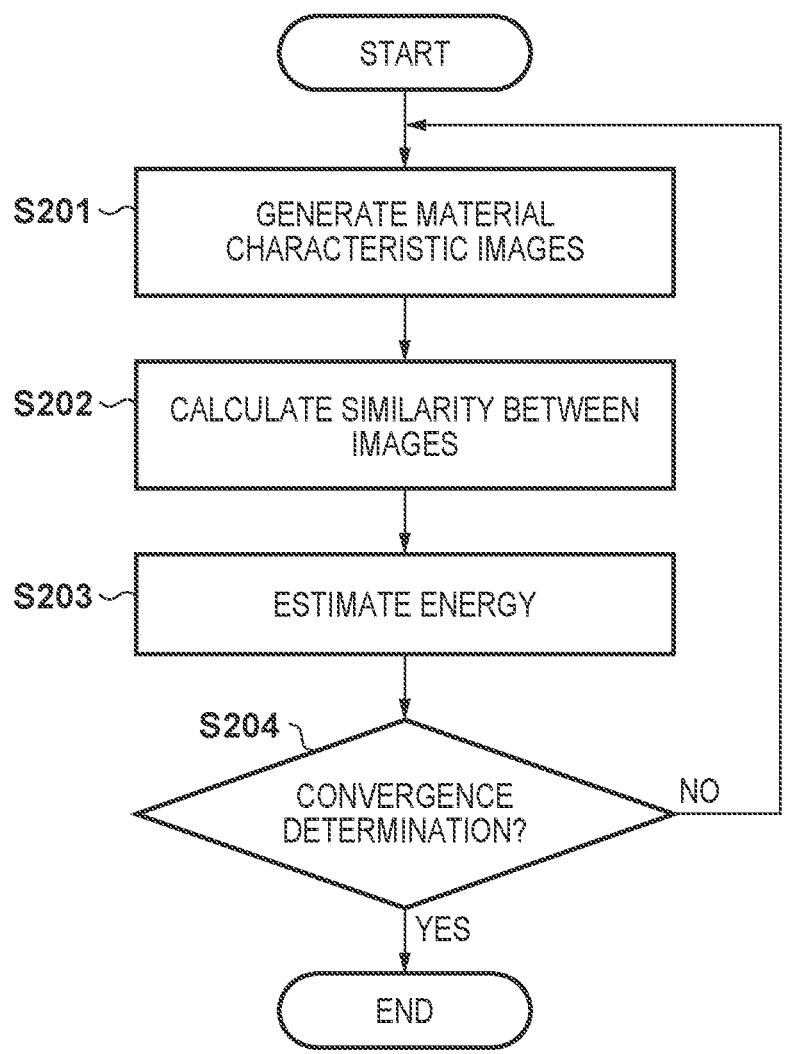
FIG. 2 is a flowchart illustrating processing by an image processing unit of the first embodiment.
Figure 3:
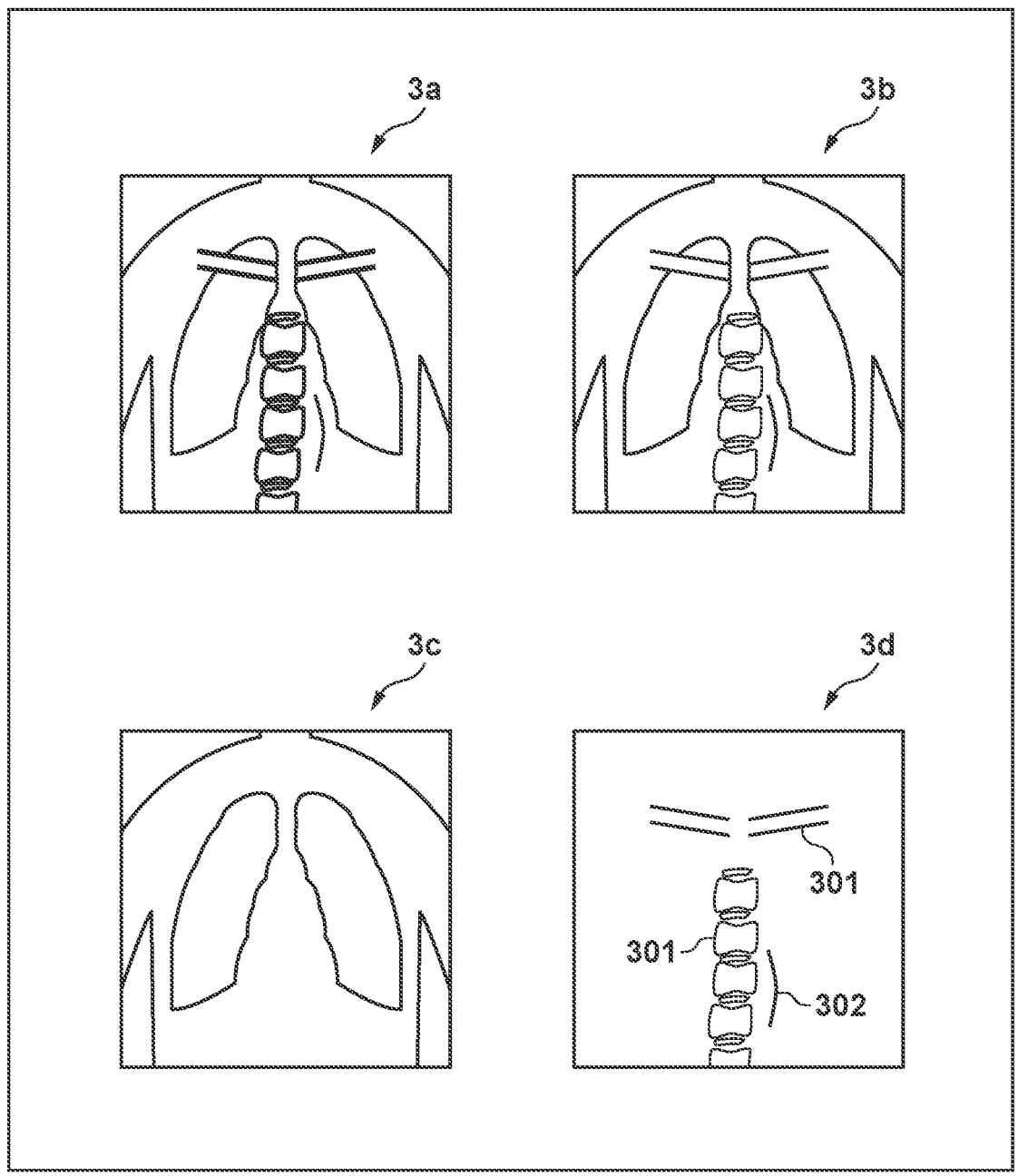
FIG. 3 is a schematic diagram of radiation images and material characteristic images in the first embodiment.

Next, the processing in the image processing unit 109 of the first embodiment will be described in detail with reference to the flowchart illustrated in FIG. 2. FIG. 2 is a flowchart explaining the processing of the image processing unit 109. Further, images 3*a* and 3*b* of FIG. 3 illustrate an example of high-energy and low-energy radiation images obtained from the FPD 102, and images 3*c* and 3*d* illustrate examples of material characteristic images generated by the image processing unit 109.

The image processing unit 109 executes the processing illustrated in FIG. 2 in response to the occurrence of some trigger (for example, that an imaging condition (tube voltage, pulse width of the voltage) is changed). In step S201 to S204 of FIG. 2, the image processing unit 109 generates material characteristic images (image 3*c*, image 3*d*) using a high-energy radiation image $XH_n$ (image 3*a*) and a low-energy radiation image $XL_n$ (image 3*b*). Based on the degree of similarity between the material characteristic image generated before the occurrence of the trigger (first timing) and the material characteristic image generated this time (second timing), the image processing unit 109 estimates the energy spectrum of the tube voltage that the radiation generator 104 has applied to the radiation tube 101 or the radiation irradiated from the radiation tube 101. That is, the radiation energy at the second timing is estimated using the material characteristic image obtained at the first timing as a reference image. Hereinafter, each step will be described in detail.

First, in step S201, the material characteristic calculation unit 110 generates material characteristic images using energy subtraction. The material characteristic calculation unit 110 calculates the attenuation characteristics of high-energy and low-energy radiation using the following [Equation 1] and [Equation 2].

$$I_H = \frac{\int n_H(E) E e^{-\mu_A(E) d_A - \mu_C(E) d_C} dE}{\int n_H(E) E dE} \quad \text{[Equation 1]}$$

$$I_L = \frac{\int n_L(E) E e^{-\mu_A(E) d_A - \mu_C(E) d_C} dE}{\int n_L(E) E dE} \quad \text{[Equation 2]}$$

Here, $I_H$ represents the attenuation characteristic of high-energy radiation and $I_L$ represents the attenuation characteristic of low-energy radiation. $n_H(E)$ represents the energy spectrum of high-energy radiation irradiated to the subject, and $n_L(E)$ represents the energy spectrum of low-energy radiation irradiated onto the subject. The energy spectrum may be measured in advance by a spectrometer or the like or obtained by simulation. E is a variable representing energy. Also, $\mu_A(E)$ is the ray attenuation coefficient of a soft material, and $\mu_C(E)$ is the ray attenuation coefficient of a contrast agent. Also, $d_A$ represents the thickness of the soft material, and $d_C$ represents the thickness of the contrast agent.

The material characteristic calculation unit 110 obtains the soft material thickness $d_A$ and the contrast agent thickness $d_C$ such that the attenuation characteristic $I_H$ of the high-energy radiation illustrated in [Equation 1] matches the pixel value of the high-energy radiation image $XH_n$ (image 3a in FIG. 3) and the attenuation characteristic $I_L$ of the low-energy radiation illustrated in [Equation 2] matches the pixel value of the low-energy radiation image $XL_n$ (image 3b in FIG. 3). Although any known technique may be used for this calculation, an example using the Newton-Raphson method, which is one of the successive approximation methods, will be described in the present embodiment. Specifically, by repeating the calculation in accordance with the following [Equation 3], the soft material thickness $d_A$ and the contrast agent thickness $d_C$ are determined. In [Equation 3], k represents the number of iterations.

$$\begin{pmatrix} d_A^{k+1} \\ d_C^{k+1} \end{pmatrix} = \begin{pmatrix} d_A^k \\ d_C^k \end{pmatrix} - \begin{pmatrix} \frac{\partial I_H^k}{\partial d_A} & \frac{\partial I_H^k}{\partial d_C} \\ \frac{\partial I_L^k}{\partial d_A} & \frac{\partial I_L^k}{\partial d_C} \end{pmatrix} \begin{pmatrix} I_H^k - XH_n \\ I_L^k - XL_n \end{pmatrix} \quad \text{[Equation 3]}$$

By performing this calculation on all the pixels of the high-energy radiation image $XH_n(i, j)$ and the low-energy radiation image $XL_n(i, j)$, a soft material thickness image $d_{An}(i, j)$ (image 3c in FIG. 3) and a contrast agent thickness image $d_{Cn}(i, j)$ (image 3d in FIG. 3), which are material characteristic images, are obtained. Here, i and j denote coordinates in the row direction and the column direction of the image, respectively. Note that, in the present embodiment, material separation is performed for the thickness of a soft material and a contrast agent, but the present invention is not limited thereto, and it is also possible to perform material separation for the thickness of any other material, for example, a soft material and a bone. When material separation is performed for a soft material and a contrast agent using two radiation energies, a bone 301 and a contrast agent 302 are separated into the same material characteristic image as in the image 3d.

In step S202, the similarity calculation unit 111 calculates an index of similarity between the material characteristic images. In this embodiment, a case is considered where there was a change in the shooting angle in the 61st moving image frame (hereinafter, described as moving image frame 61), whereby the ABC function is activated, the imaging conditions are changed, and the pulse width of the high-energy radiation is shortened to about 4 msec. At this time, the waveform of the actual tube voltage applied from the radiation generator 104 to the radiation tube 101 is as illustrated by the solid line in FIG. 4. That is, bluntness occurs in the rise and fall of the tube voltage due to the impedance of a high-voltage cable or the like connecting between the radiation tube 101 and the radiation generator 104, and thereby, it becomes impossible to apply a predetermined tube voltage as in the solid-line waveform in FIG. 4. As a result, the tube voltage and the effective tube voltage are different.

Figure 4:
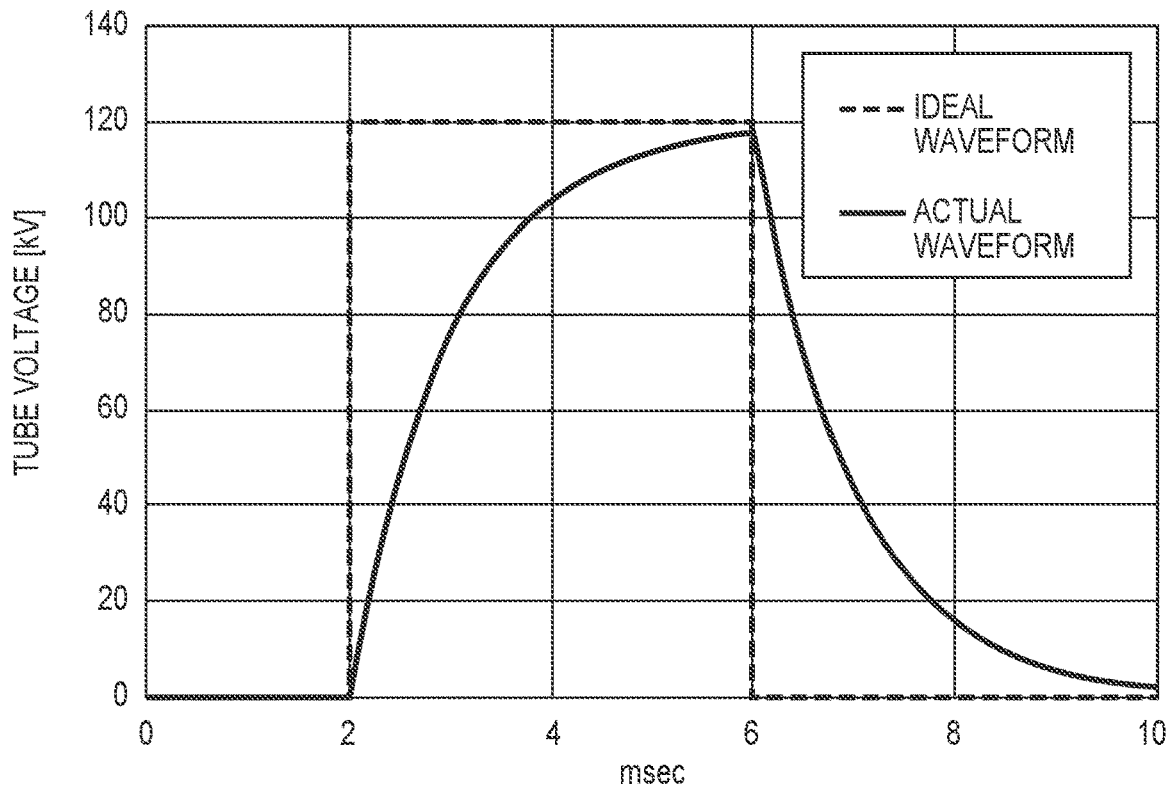
FIG. 4 is a diagram illustrating a high voltage pulse of a radiation tube in the first embodiment.

In such a state, the high-energy radiation energy spectrum $n_H(E)$ will not be the energy spectrum at 120 kV of the ideal waveform illustrated by the dashed line in FIG. 4. It also becomes difficult to specify the energy spectrum itself, because the state is such that the tube voltage changes transiently. In addition, since it is generally desirable that the high-energy radiation and the low-energy radiation have the same irradiation dose, the pulse width of the high-energy radiation is likely to become shorter in order to lower the irradiation dose.

The similarity calculation unit 111 calculates the similarity of the material characteristic images between a moving image frame 60 which is the material characteristic image generated in step S201 at the first timing and the moving image frame 61 which is the material characteristic image generated in step S201 at the second timing. Specifically, for example, the index of the similarity is calculated using the sum of least-squares differences (SSD) as illustrated in the following [Equation 4].

$$SSD = \sum_{i,j}^{w,h} (d_{c60}(i, j) - d_{c61}(i, j))^2 \quad \text{[Equation 4]}$$

Here, w and h are the number of pixels in the horizontal direction and the number of pixels in the vertical direction, respectively, of the image. Further, although SSD is calculated using the contrast agent thickness $d_C$ as a material characteristic image, the soft material thickness $d_A$ may be used. Note that the thickness of the contrast agent is used in this embodiment because the thickness of the contrast agent includes the thickness of a bone which does not change in thickness and in which body movement is relatively unlikely to occur. As long as an image in which bone is separated is obtained as a material characteristic image, the thickness of bone may be used for calculation of [Equation 4].

In step S203, the energy estimation unit 112 estimates the radiation energy such that the similarity between the material characteristic images is the highest. That is, in the present embodiment, the following optimization operation is performed, for example, in order to search for the radiation energy that minimizes the sum of least-squares differences (SSD) of [Equation 4].

First, the calculated tube voltage of high-energy radiation is changed by $\Delta H$ from H. Although the magnitude of $\Delta H$ is arbitrary, it is set to 0.5 kV in the present embodiment. As a result, the attenuation characteristic of high-energy radiation will be as expressed by [Equation 5]. $n_{H+\Delta H}(E)$ is the radiation energy spectrum at tube voltage=H+$\Delta H$.

$$I_{H+\Delta H} = \frac{\int n_{H+\Delta H}(E) E e^{-\mu_A(E)\delta_A - \mu_C(E)\delta_C} dE}{\int n_{H+\Delta H}(E) E dE} \quad \text{[Equation 5]}$$

Further, the soft material thickness $\delta_A$ and the contrast agent thickness $\delta_C$ are sequentially obtained by repeating the calculation in accordance with the following [Equation 6] using the material characteristic calculation unit 110.

$$\begin{pmatrix} \delta_A^{k+1} \\ \delta_C^{k+1} \end{pmatrix} = \begin{pmatrix} \delta_A^k \\ \delta_C^k \end{pmatrix} - \begin{pmatrix} \frac{\partial I_{H+\Delta H}^k}{\partial d_A} & \frac{\partial I_{H+\Delta H}^k}{\partial d_C} \\ \frac{\partial I_L^k}{\partial d_A} & \frac{\partial I_L^k}{\partial d_C} \end{pmatrix} \begin{pmatrix} I_H^k - XH_{61} \\ I_L^k - XL_{61} \end{pmatrix} \quad \text{[Equation 6]}$$

The contrast agent thickness $\delta_C$ obtained here should be approximately close to $d_C$ if the same subject is captured in the moving image frame 60 and the moving image frame 61. This is because, even if the subject moves, the heart beats, they breathe, or the contrast agent flows, the main bone 301 illustrated in the image 3d of FIG. 3 does not change much between the frames. Therefore, if the following [Equation 7] is calculated by the similarity calculation unit 111 such that $SSD_M$ becomes the smallest, the effective tube voltage can be estimated. The effective tube voltage here means the tube voltage that provides the energy of the radiation irradiated in the actual waveform of FIG. 4.

$$SSD_M = \sum_{i,j}^{w,h} (d_{c60}(i,j) - \delta_{c61}(i,j))^2 \quad [\text{Equation 7}]$$

In the present embodiment, the energy estimation unit 112 searches for radiation energy such that the similarity calculated by the similarity calculation unit increases. For example, the energy estimation unit 112 searches for the radiation energy that maximizes the similarity using an optimization technique. In the present embodiment, the gradient method is used as the optimization method, but the present invention is not limited to this, and for example, a Newton method, a bisection method, or the like may be used. Using the gradient method, the estimated tube voltage $H_E$ is expressed by [Equation 8] below. Where $\alpha$ is the coefficient for adjusting the convergence of the gradient method.

$$H_E = H - \alpha \frac{SSD - SSD_M}{\Delta H} \quad [\text{Equation 8}]$$

In step S204, the image processing unit 109 performs convergence determination. If the convergence determination is NO, the energy estimation unit 112 sets the tube voltage $H_E$ estimated in step S203 as a new tube voltage H, returns to step S201, and repeats the process of steps S201 to S203. That is, the energy estimation unit 112 calculates SSD for the new tube voltage H (step S201), calculates $SSD_M$ by changing the new tube voltage H by $\Delta H$ (step S202), and calculates the tube voltage $H_E$ (estimated) by [Equation 8].

Incidentally, the convergence condition of the optimization method used in the convergence determination of step S204 includes, for example, that the similarity represented by the index has exceeded a threshold value, that the change in similarity has entered a predetermined range, and that the process was executed for a preset number of loops. That the similarity has exceeded the threshold value is, for example, that the sum of least squares $SSD_M$ represented by [Equation 7] has become sufficiently smaller (that $SSD_M$ has become less than the threshold value). That the change in similarity has entered a predetermined range is, for example, |SSD-$SSD_M$| has become sufficiently smaller. The process was executed for a preset number of loops since, for example, the loop from step S201 to step S203 has been repeated a predetermined number of times. It is determined that convergence has occurred when any of these convergence conditions are satisfied.

If it is determined that convergence has occurred in step S204 (if convergence determination is YES), the energy estimation unit 112 sets the tube voltage $H_E$ obtained by the calculation of [Equation 8] as the estimated tube voltage and then terminates the processing. This estimated tube voltage $H_E$ is the effective tube voltage corresponding to the actual voltage waveform illustrated in FIG. 4, and the energy spectrum $n_{HE}$ of this estimated tube voltage $H_E$ corresponds to the effective energy spectrum of the radiation having the actual voltage waveform illustrated in FIG. 4.

Figure 5:
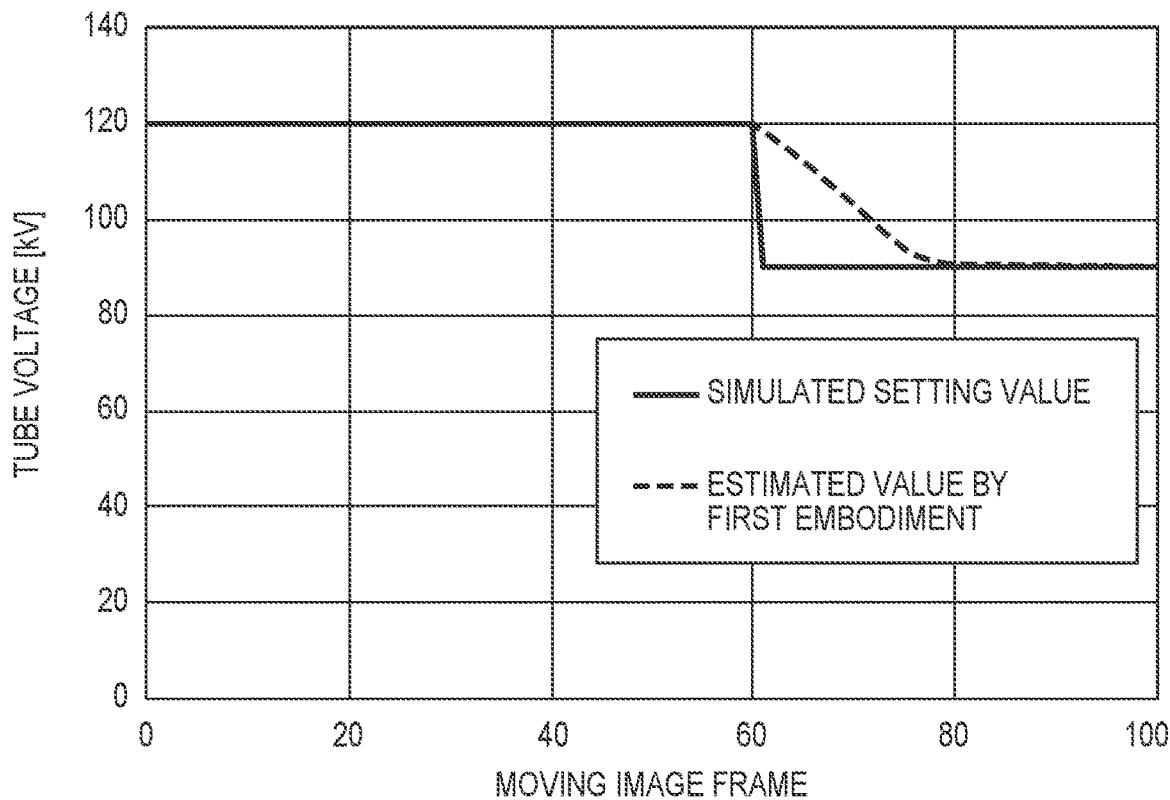
FIG. 5 is a diagram illustrating a simulated result of the first embodiment.

FIG. 5 is a simulation result illustrating the effect of estimation of the tube voltage according to the present embodiment. In this simulation, a high-energy radiation image $XH_n$ and a low-energy radiation image $XL_n$ are obtained by irradiating X-rays with a tube voltage of high-energy radiation of 120 kV and a tube voltage of low-energy radiation of 70 kV to a numerical phantom composed of a soft material, a contrast agent, and a bone simulating a human body. The material characteristic calculation unit 110 sequentially generates a thickness image $d_{An}$ of the soft material and a thickness image $d_{Cn}$ of the contrast agent by the step S201 calculation from the high-energy radiation image $XH_n$ and the low-energy radiation image $XL_n$. In this simulation, the tube voltage of high energy radiation is intentionally changed to 90 kV in the moving image frame 61. In such a condition, tube voltages are estimated by performing the processing of the steps S202 and S203.

In this simulation, the convergence determination (step S204) is not performed, and steps S201 to S203 are not looped. That is, the estimated value of the tube voltage obtained by performing the process of steps S201 to S203 once is illustrated. As illustrated in FIG. 5, it can be seen that the estimated value of the tube voltage according to the first embodiment begins to gradually approach the simulated setting value starting from the moving image frame 61 and approximately coincides with the simulated setting value of 90 kV at around a moving image frame 80. If convergence determination (S204) is performed as illustrated in FIG. 2 and the looping of the process of steps S201 to S203 is performed sufficiently, the estimated value of the tube voltage can be made to be 90 kV in the moving image frame 61. However, since a sufficient number of loops are required in order to obtain an accurate estimation value, it is necessary to set the number of loops in consideration of the processing speed of a moving image to be obtained.

The process of steps S201 to S204 is thus an estimation of an effective tube voltage, that is, the energy spectrum, according to the present embodiment. In the embodiment described above, this processing is started with the occurrence of some event as a trigger but may be always executed during X-ray fluoroscopic imaging. Further, an event for starting the process of estimating the radiation energy includes, for example, the control unit 105 receiving a notification of a change in imaging conditions (e.g., at least one of tube voltage (kV), tube current (mA), pulse width (msec)) from the radiation generator 104.

Alternatively, another example of an event for starting the process of estimating the radiation energy is detecting degradation (change in image quality) of the material characteristic image generated by the material characteristic calculation unit 110. For example, it is possible to determine whether or not the degradation of the material characteristic image has occurred based on whether or not the SSD calculated by [Equation 4] has changed beyond a predetermined threshold value. Further, when calculating the SSD using [Equation 4] in order to detect the occurrence of degradation of the material characteristic image, the comparison is not limited to that with the material characteristic image of the current frame, and comparison for the similarity with the material characteristic image of a frame preceding by a predetermined number may be performed.

In the process of estimating the radiation energy, the material characteristic image obtained at the first timing is used as a reference, and the radiation energy is estimated such that the material characteristic image obtained at the second timing after the first timing is similar to the reference. This is the same in the case where the process of estimating the radiation energy is always performed during fluoroscopic imaging or is performed in response to a trigger. In the above embodiment, the material characteristic image immediately before the occurrence of the event (the moving image frame 60 in the above embodiment) is used as the reference, but the material characteristic image used as the reference is not limited to this. The material characteristic image obtained at an arbitrary timing before the occurrence of the event can be used as a reference. When the estimation of radiation energy is always performed during shooting, it is also conceivable to use the material characteristic image of the immediately preceding frame as a reference, to use the material characteristic image calculated by the exact radiation energy obtained at any timing during shooting as a reference, or the like.

Further, a calculation of similarity indicated in [Equation 7] may be performed for a set region (ROI (region of interest)). For example, the mediastinum portion moves greatly due to the heart beating, the diaphragm moving due to respiration, and the like. The tube voltage can be estimated more accurately by excluding a portion that moves significantly during moving image shooting, such as the mediastinum portion, from the region (ROI) for calculating the similarity. To realize this processing, for example, the energy estimation unit 112 excludes from the region for calculating the similarity portions whose pixel value fluctuates between the frames of the radiation image (which may be a high-energy radiation image or a low-energy radiation image) more than a predetermined threshold value. This predetermined threshold value may be such that the user can set it via the user interface. Alternatively, a user interface may be provided to allow an operator, such as a physician or a radiologist, to specify on the monitor 116 a region (ROI) for calculating the similarity.

Further, in the above-described embodiment, the similarity calculation unit 111 searches for the tube voltage that maximizes the similarity by the gradient method using the tube voltage included in the imaging conditions notified from the radiation generator as the initial value. However, the present invention is not limited to this, and an effective tube voltage may be estimated from the notified imaging conditions and used as an initial value. For example, the similarity calculation unit 111 may roughly estimate the effective tube voltage from the tube voltage and the pulse width included in the imaging conditions and, using this as the initial value, estimate the tube voltage that maximizes the similarity by the gradient method. By setting the initial value more appropriately, the processing time until the convergence condition of the gradient method is satisfied and the processing amount can be reduced. For example, the material characteristic calculation unit 110 has a table in which an effective tube voltages are registered in accordance with the imaging conditions which include the tube voltage and the pulse width and generates a material characteristic image using an effective tube voltage obtained from the table based on the notified imaging conditions. Since the similarity calculation unit 111 can estimate the tube voltage that maximizes the similarity with the above-described method using as the initial value the effective tube voltage obtained from the table, it is possible to obtain the result of estimation of the radiation energy more quickly.

In addition, since the material characteristic images are generated by changing the tube voltage from H by ΔH in step S203, a radiation energy spectrum corresponding to the changed tube voltage is required. In order to support this, the radiation energy may be measured in advance by changing the tube voltage in increments of ΔH and then held, for example. Alternatively, for example, the energy estimation unit 112 may calculate, using an approximate expression, the radiation spectrum corresponding to the changed tube voltage and then use it.

As described above, according to the first embodiment, the tube voltage can be estimated in real time using the similarity between the material characteristic images. This makes it possible to stably perform energy subtraction even when the tube voltage fluctuates due to ABC (auto brightness control) or the like during imaging at the time of extracting a contrast-enhanced blood vessel using the energy subtraction technique in a vascular imaging apparatus.

Second Embodiment

In the first embodiment, an iterative calculation such as the Newton-Raphson method is used for the calculation of the material characteristic image. In the second embodiment, by approximating each of the plurality of types of energies to a monochromatic energy, a material characteristic image is obtained easily without using iterative calculations. The configuration of the radiation imaging system 100 of the second embodiment is the same as that of the first embodiment (FIG. 1). In the following description, descriptions of parts that are the same as those of the first embodiment will be omitted, and components specific to the second embodiment will be mainly described.

The processing in the image processing unit 109 of the second embodiment will be described in detail with reference to the flowchart in FIG. 6. The control unit 105 stores the radiation image captured by the FPD 102 in the storage unit 108 and transfers the radiation image to the image processing unit 109.

In step S601, the material characteristic calculation unit 110 approximates the radiation energy spectrum in [Equation 1] and [Equation 2] of the first embodiment to the monochromatic energy with $n_H(E)=\delta(E_H)$ and $n_L(E)=\delta(E_L)$. Note that δ is a Dirac δ function. Here, $E_H$ and $E_L$ are representative values of the energy spectrum, and for example, the average energy or the peak position value of the spectrum can be used. Thus [Equation 1], [Equation 2] will become the following [Equation 9], [Equation 10], respectively.

$$I_H = e^{-\mu_A(E_H)d_A - \mu_C(E_H)d_C} \quad \text{[Equation 9]}$$

$$I_L = e^{-\mu_A(E_L)d_A - \mu_C(E_L)d_C} \quad \text{[Equation 10]}$$

Further, by performing logarithmic conversion on [Equation 9] and [Equation 10], [Equation 11] and [Equation 12] are obtained.

$$-\ln I_H = \mu_A(E_H)d_A + \mu_C(E_H)d_C \quad \text{[Equation 11]}$$

$$-\ln I_L = \mu_A(E_L)d_A + \mu_C(E_L)d_C \quad \text{[Equation 12]}$$

The soft material thickness $d_A$ and the contrast agent thickness $d_C$ expressed by [Equation 11] and [Equation 12] are obtained by the following [Equation 13].

$$\begin{pmatrix} d_A \\ d_B \end{pmatrix} = \begin{pmatrix} \mu_A(E_H) & \mu_C(E_H) \\ \mu_A(E_L) & \mu_C(E_L) \end{pmatrix}^{-1} \begin{pmatrix} -\ln I_H \\ -\ln I_L \end{pmatrix} \quad \text{[Equation 13]}$$

As described above, since according to the second embodiment the numerical integration of [Equation 1] and [Equation 2] and the iterative calculation of [Equation 3] of the first embodiment will become unnecessary, it is possible to calculate the material characteristic image at a higher speed than that of the first embodiment. The processing of steps S602, S603, and S604 is respectively the same as the processing of steps S202, S203, and S204 in the first embodiment (FIG. 2). Through the above processing, $E_H$ and $E_L$ can be estimated in real time using the similarity between the material characteristic images without using the reference. This makes it possible to stably perform energy subtraction even when the tube voltage fluctuates due to ABC (auto brightness control) or the like during imaging, for example, when using the energy subtraction technique in a vascular imaging apparatus.

To facilitate understanding, in each of the above embodiments the case has been described in which only the energy of the high-energy radiation has changed; however, the case where the energy of the low-energy radiation or the high-energy radiation and low-energy radiation has changed can be similarly estimated. If the energies of the high-energy radiation and the low-energy radiation change simultaneously, the tube voltages of each of the high-energy radiation and the low-energy radiation may be varied by ΔH to search for the radiation energy that provides the maximum degree of similarity.

Further, in each of the above embodiments, an example in which the present invention is applied to radiation moving image capturing such as X-ray fluoroscopic imaging has been described, but the present invention can also be applied to radiation still image capturing. For example, when capturing a plurality of still images while changing the radiation energy, if a reference material characteristic image is obtained in advance, the radiation energy in each still image shooting can be estimated, and an accurate material characteristic image can be obtained.

According to the present invention, it is possible to perform stable energy subtraction by improving the accuracy of the energy (spectrum) of radiation used in energy subtraction.

Other Embodiments

Note that the present invention is not limited to the above-described embodiments, and various changes and modifications can be made without departing from the scope of the present invention. The present invention can adopt an embodiment in the form of, for example, a system, apparatus, method, program, or storage medium. More specifically, the present invention may be applied to a system constituted by a plurality of apparatuses, or an apparatus comprising a single device.

Embodiment(s) of the present invention can also be realized by a computer of a system or apparatus that reads out and executes computer executable instructions (e.g., one or more programs) recorded on a storage medium (which may also be referred to more fully as 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An image processing apparatus comprising:
a generation unit configured to generate a material characteristic image based on a plurality of radiation images corresponding to a plurality of radiation energies; and
an estimation unit configured to estimate at least one of the plurality of radiation energies at a second timing using a plurality of material characteristic images including a material characteristic image that the generation unit generated based on a plurality of radiation images acquired at a first timing and a material characteristic image that the generation unit generated based on a plurality of radiation images acquired at the second timing later than the first timing.

2. The image processing apparatus according to claim 1, wherein the estimation unit estimates at least one of the plurality of radiation energies at the second timing using a similarity of the plurality of material characteristic images.

3. The image processing apparatus according to claim 2, wherein the similarity uses, as an index, a sum of squared differences, a sum of absolute differences, or a cross-correlation between the material characteristic image generated at the first timing and the material characteristic image generated at the second timing.

4. The image processing apparatus according to claim 1, wherein the generation unit generates a material characteristic image using a radiation energy of an effective tube voltage acquired based on imaging conditions at the second timing from a table in which effective tube voltages corresponding to imaging conditions including tube voltage and pulse width are registered.

5. The image processing apparatus according to claim 4, wherein the estimation unit searches for a radiation energy using the effective tube voltage that the generation unit acquired as an initial value such that the similarity between the plurality of material characteristic images becomes larger.

6. The image processing apparatus according to claim 1, wherein the material characteristic image is an image of a thickness of at least a soft material, a bone, or a contrast agent.

7. The image processing apparatus according to claim 2, wherein the estimation unit searches for a radiation energy maximizes the similarity by an optimization method.

8. The image processing apparatus according to claim 7, wherein a convergence condition for the search by the optimization method is any of that the similarity has exceeded a threshold value, that a change in the similarity has entered a predetermined range, and that a loop has been executed a preset number of times met.

9. The image processing apparatus according to claim 1, wherein the estimation unit starts estimating a radiation energy at the second timing in accordance with a change in an imaging condition including at least one of a tube voltage, a tube current, and a pulse width, and the first timing is a timing that is before an occurrence of the change of the imaging condition.

10. The image processing apparatus according to claim 1, wherein the estimation unit starts estimating a radiation energy at the second timing in accordance with a detection of degradation of a material characteristic image generated by the generation unit, and the first timing is a timing that is before the detection of the degradation.

11. The image processing apparatus according to claim 1, wherein the estimation unit performs an estimation of radiation energy at the second timing for each frame of a radiation image.

12. The image processing apparatus according to claim 1, further comprising a setting unit configured to set in the plurality of material characteristic images a region for calculating a similarity between the plurality of material characteristic images.

13. The image processing apparatus according to claim 12, wherein the setting unit sets as a region for calculating the similarity a region from which a pixel whose fluctuation of a pixel value between frames of a radiation image is larger than a threshold value has been excluded.

14. The image processing apparatus according to claim 12, wherein the setting unit sets a region for calculating the similarity in accordance with a specification of a region by a user.

15. The image processing apparatus according to claim 1, wherein the generation unit acquires a thickness of a specific material by solving a non-linear simultaneous equation obtained based on a radiation attenuation of a specific material corresponding to at least two types of radiation energy and a radiation image corresponding to at least two types of radiation energy.

16. The image processing apparatus according to claim 15, wherein the generation unit respectively approximates the at least two types of radiation energy to a monochromatic energy and solves the non-linear simultaneous equation.

17. The image processing apparatus according to claim 1, wherein the estimation unit estimates at least one of the plurality of radiation energies at the second timing by searching for a radiation energy such that a similarity of the plurality of material characteristic images becomes larger.

18. A radiography apparatus comprising:
a radiation detection unit configured to capture a plurality of radiation images corresponding to a plurality of radiation energies;
a generation unit configured to generate a material characteristic image based on the plurality of radiation images captured by the radiation detection unit; and
an estimation unit configured to estimate at least one of the plurality of radiation energies at a second timing using a plurality of material characteristic images including a material characteristic image that the generation unit generated based on the plurality of radiation images that the radiation detection unit acquired at a first timing and a material characteristic image that the generation unit generated based on the plurality of radiation images that the radiation detection unit acquired at the second timing later than the first timing.

19. A method of controlling an image processing apparatus, the method comprising:
generating a material characteristic image based on a plurality of radiation images corresponding to a plurality of radiation energies; and
estimating at least one of the plurality of radiation energies at a second timing using a plurality of material characteristic images including a material characteristic image generated in the generating based on a plurality of radiation images acquired at a first timing and a material characteristic image generated in the generating based on a plurality of radiation images acquired at the second timing later than the first timing.

20. A non-transitory computer-readable storage medium storing a program for causing a computer to execute the method according to claim 19.

* * * * *